(12) United States Patent
Tripathi et al.

(10) Patent No.: US 7,039,527 B2
(45) Date of Patent: May 2, 2006

(54) METHOD FOR MEASURING DIFFUSIVITIES OF COMPOUNDS USING MICROCHIPS

(75) Inventors: Anubhav Tripathi, Marlborough, MA (US); Josh Molho, Fremont, CA (US)

(73) Assignee: Caliper Life Sciences, Inc., Mountain View, CA (US)

(*) Notice: Subject to any disclaimer, the term of this patent is extended or adjusted under 35 U.S.C. 154(b) by 0 days.

(21) Appl. No.: 10/956,211

(22) Filed: Sep. 30, 2004

(65) Prior Publication Data

US 2005/0182573 A1 Aug. 18, 2005

Related U.S. Application Data

(60) Provisional application No. 60/507,740, filed on Oct. 1, 2003.

(51) Int. Cl.
*G06F 19/00* (2006.01)

(52) U.S. Cl. ........................ 702/27; 73/64.47
(58) Field of Classification Search ............... 702/27, 702/30, 138, 142, 179, 180–182; 73/1.02, 73/1.17, 1.35, 1.37, 1.57, 54.01, 54.02, 54.07, 73/54.09, 54.13, 861, 488, 861.08, 504.05, 73/64.47; 436/514
See application file for complete search history.

(56) References Cited

U.S. PATENT DOCUMENTS 5,974,867 A 11/1999 Forster et al.
2002/0046948 A1* 4/2002 Chow et al. ............. 204/450

FOREIGN PATENT DOCUMENTS

WO    WO-01/02850 A1    1/2001

OTHER PUBLICATIONS

Bello, et al., "Use of Taylor-Aris Dispersion for Measurement of Solute Diffusion Coefficient in Thin Capillaries," SCIENCE, vol. 266, Nov. 4, 1994, pp. 773-776.
Belongia, et al., "Measurement on the Diffusion Coefficient of Colloidal Particles by Taylor-Aris Dispersion," Journal of Colloid and Interface Science, vol. 195, 1997, pp. 19-31.

* cited by examiner

*Primary Examiner*—Edward Raymond
(74) *Attorney, Agent, or Firm*—Donald R. McKenna; Ann C. Peterson (57) ABSTRACT

A method for determining the molecular diffusivity of a solute in a microchannel where a solute is introduced into a first end of a microchannel and a first concentration profile is measured at first and second locations along the microchannel. A theoretical concentration profile can be calculated at the second location based on the measured first concentration profile at the first location. The molecular diffusivity can be found by minimizing the error when comparing the theoretical concentration profile to the measured second concentration profile. Further, this technique allows for average velocity to be measured simultaneously with molecular diffusivity.

10 Claims, 4 Drawing Sheets

METHOD FOR MEASURING DIFFUSIVITIES OF COMPOUNDS USING MICROCHIPS

BACKGROUND OF THE INVENTION

This invention relates to a method for calculating the molecular diffusivity of a solute in a channel, such as a capillary, tube or microfluidic channel. More particularly, this invention relates to calculating molecular diffusivity of a solute using Taylor dispersion concepts.

Recent efforts have been directed towards the development of microscale assay methods in which various chemical and biological processes may be examined in rapid succession and with small amounts of material. Such microscale assay methods can be carried out in, for example, microfluidic devices. A typical microfluidic device, which can be fabricated from a glass, silica or plastic substrate, contains a network of microscale channels through which fluids and chemicals are moved in order to perform an assay. These devices use minute quantities of fluids or other materials, controllably flowed and/or directed, to generate highly reproducible and rapidly changeable microenvironments for control of chemical and biological reaction conditions, enzymatic processes, etc.

Microfluidic devices use small volumes of material. A plug containing the material of interest, such as a molecule (e.g. a protein or DNA molecule), compound, or biological compound is introduced into a microscale channel and observed at least at some point along the channel. Several plugs of a variety of compounds are typically introduced into the same channel, the various plugs being separated by sufficient solvent or buffer material to distinguish adjacent plugs. However, as a plug of material moves along a channel, the material of interest in the plug tends to disperse from the plug into adjacent volumes of solvent or buffer that separate the plug of material from adjacent sample plugs. Such dispersion results from the laminar or parabolic velocity profile of a plug of material in a channel coupled with the molecular diffusivity of the particular material within a particular solvent or buffer. Due to dispersion, a plug of material having a certain length and a certain concentration upon entering a channel will have a longer length and be less concentrated after it travels through the channel.

One advantage of microfluidic devices is that a large variety of small plugs can be introduced and monitored within a channel in rapid succession. The more frequently plugs of material are directed into a channel, the more tests can be run in a smaller amount of time. If the plugs of material are introduced too closely, however, dispersion may cause the solute in one sample plug to overlap the solute in a second adjacent sample plug by the time the plugs travel to the opposite end of the channel. Typically, a detector mechanism is placed at this opposite end to measure a property of each plug of material. Thus, it is helpful to be able to adequately predict how the length of a plug will increase due to dispersion to maximize throughput (i.e., a maximum number of different samples plugs introduced to the channel in a minimum amount of time) and minimize cross-contamination of adjacent sample plugs. If one can predict the amount of dispersion, one can modify the dimensions of the microfluidic device or the process parameters to maximize throughput. One method for maximizing throughput that depends on an accurate prediction of dispersion is discussed in U.S. Pat. No. 6,150,119, which is incorporated herein by reference. In order to accurately predict the dispersion of a sample material, it is necessary to accurately determine the molecular diffusivity of that sample material.

The mathematics of diffusion and dispersion in long thin channels is well understood. Sir Geoffery Taylor developed a method to determine molecular diffusion based on the mass flux in a capillary tube. Taylor's methods are discussed in Taylor, Sir Geoffery, F. R. S. "Conditions of soluble matter in solvent flowing slowly through a tube," *Proceedings of the Royal Society of London, Series A*, 219, 186–203 (1953), and Taylor, Sir Geoffrey, F. R. S., "Conditions under which dispersion of a solute in a stream of solvent can be used to measure molecular diffusion," *Proceedings of the Royal Society of London, Series A*, 225, 473–477 (1954), both of which are incorporated herein by reference. In particular, Taylor determined that the mass flux along the length of a capillary tube is a sum of convection forces and molecular diffusion. Although dispersion results from a combination of convection and diffusion, the same type of equations that describe diffusion alone can describe the phenomenon of dispersion. Rutherford Aris developed a formula based on the work of Taylor for calculating a dispersion coefficient K. The derivation of that formula is disclosed in Aris, R., "On the dispersion of a solute in a fluid flowing through a tube," *Proceedings of the Royal Society of London, Series A*, 235, 67–77 (1956), which is incorporated herein by reference. The formula for the Taylor-Aris dispersion coefficient in a channel with a circular cross-section is:

$$K = D\left(1 + \frac{U^2 r^2}{48 D^2}\right)$$

where U is the mean velocity of the sample plug, r is the radius of the capillary tube, and D is the coefficient of molecular diffusion. This formula must be modified to predict the dispersion coefficient in channels with non-circular cross-sections. The following formula was developed for calculating the dispersion coefficient in a channel with a rectangular cross-section:

$$K = D\left(1 + \frac{1}{210} f\left(\frac{d}{w}\right) \frac{U^2 d^2}{D^2}\right)$$

where the function $f(d/w)$ is a known function of the depth d and width w of the channel, U is the average velocity and D is the molecular diffusivity. A detailed derivation of this formula is in Chatwin, P. C. and P. J. Sullivan, "The effect of aspect ratio on longitudinal diffusivity in rectangular channels," *Journal of Fluid Mechanics*, 120, 347–358 (1982), which is incorporated herein by reference.

When a sample plug consisting of a sharp pulse of material is inserted into a stream of fluid flowing through a channel, the concentration profile of the plug will change as it travels down the length of the channel. Material will disperse both in front of and behind the boundaries of the original plug of material. Accordingly, the concentration profile of the material observed at a point downstream of the injection will not be bounded by sudden increases in concentration. Instead, the observed concentration profile will start off at a small concentration as the beginning of the plug crosses the detection point, increasing to a peak as more particles cross the detection point, and decreasing again to a small concentration as the last particles cross the detection point. Consequently, the overall concentration profile will have the appearance of a Gaussian curve.

The approximately Gaussian concentration profile of a plug of material can be modeled using the Green's function solution to the one-dimensional diffusion equation. The Green's function solution is expressed as:

$$G(x, t, D) = \frac{1}{\sqrt{4\pi Kt}} \exp\left(\frac{-x^2}{4Kt}\right)$$

where x is the distance from the centroid of the Gaussian curve, t is time from the insertion point to the detection point, and K is the Taylor-Aris dispersion coefficient. As the plug moves down the channel, the distance x is measured with respect to the centroid of the moving plug of material. In this model, at t=0 all of the material in the plug is at x=0. Consequently this model assumes that the plug is perfectly non-dispersed when it is introduced into the channel.

From the observed experimental Gaussian concentration profile of a plug of material dispersing in pressure-driven flow through a channel one can solve for the Taylor-Aris dispersion coefficient, K, and back out the molecular diffusivity, D, from the Taylor-Aris dispersion coefficient formula appropriate for the channel geometry. However, often the average velocity U used in calculating the Taylor-Aris dispersion coefficient must be determined based on estimated values of parameters such as viscosity and channel geometry. Further, using the Green's function without convolution requires one to assume that the plug is introduced to the channel in a perfectly non-dispersed plug.

Because the Taylor-Aris method requires making various assumptions in order to calculate the molecular diffusivity, the method is typically effective only for low velocity flow in channels with small radial dimensions. Nonetheless, the method is still often used today for measuring molecular diffusivities. Methods of calculating molecular diffusivity based on the measurement of a concentration profile at a single point in a channel have been previously described. One example is Michael S. Bello et al., "Use of Taylor-Aris Dispersion for Measurement of a Solute Diffusion Coefficient in Thin Capillaries," *Science*, 266, 773–776 (1994). Measuring concentration only at a single point does not provide an accurate assessment of the change of a plug of material over the length of the channel. Also, these single point methods require extra steps to determine velocity.

Still others have calculated molecular diffusivities by measuring the concentration of a stream of solute in a microchannel. One example of such a method is discussed in Andrew E. Kamholz et al., "Optical Measurement of Transverse Molecular Diffusion in a Microchannel," *Biophys J*, 80(4), 1967–1972 (April 2001). However, this requires a fairly large sample of the solute in order to create a constant stream and is not suitable when only small volumes of sample material are available. Further, the technique taught by Kamholz et al. requires complicated mathematical manipulation of data.

Thus, what is needed is a simple method for determining both the velocity and the molecular diffusivity simultaneously while using only a small volume of sample material.

BRIEF SUMMARY OF THE INVENTION

As discussed above, dispersion causes the concentration profile of a plug of material injected into a channel in the form of a sharp pulse to approach the shape of a Gaussian curve at any discrete location along the length of the channel downstream of the injection point. As the sample travels further down the channel, more dispersion will occur. Therefore, concentration profiles observed at locations closer to the insertion point of the plug (i.e., upstream) will have a higher peak and a narrower base than concentration profiles observed at locations farther along the length of the channel (i.e., downstream). Dispersion in front of and behind the plug causes the plug to grow in length, which causes the concentration profile of the plug to widen as the plug flows downstream. Also, dispersion lowers the overall concentration at any one point in the concentration profile as the plug flows downstream, resulting in lower peaks in downstream concentration profiles.

The present invention is directed to a method for calculating the molecular diffusivity of a plug of material by measuring the concentration profile at two locations downstream of the injection point. The concentration profile at each measurement location is expressed mathematically as a Gaussian curve. The average velocity of the plug of material can be calculated by measuring the time and distance between the first and second locations. In one embodiment, the concentration profile at the first location is convoluted to determine a theoretical concentration profile at the second location. A value of K can then be computed by setting the theoretical concentration profile equal to the experimentally measured concentration profile. The computed value of K, along with the measured velocity value, can be used to determine the molecular diffusivity from the appropriate expression for the Taylor-Aris dispersion coefficient.

Instead of determining a value of K by equating a theoretical and a measured second concentration profile, a value of K can be determined by estimating a value of molecular diffusivity, computing an estimated value of K from the estimated molecular diffusivity, inserting the estimated value of K into a convolution formula for the amount of error in an estimate of the measured concentration profile, and modifying the estimated value of K to minimize the error. Once the value of K corresponding to a minimum error has been determined, that value of K, along with the measured velocity value, can be used to determine the molecular diffusivity from the appropriate expression for the Taylor-Aris dispersion coefficient.

In another embodiment, the Taylor-Aris dispersion coefficient can calculated in a method that does not require convolution. As in the embodiments employing convolution calculations, the concentration profile of the plug is measured at two locations along the channel. Using the standard definition of variance, the variance for the concentration profiles can be computed. The Taylor-Aris dispersion coefficient K can be calculated by simply finding the difference in variance between the first and second concentration profiles. As in the previous embodiments, that value of K, along with the measured velocity value, can be used to determine the molecular diffusivity.

The mathematical models employed in the disclosed methods of measuring and comparing the concentration profiles of a single plug at two different locations automatically take into account such physical parameters as the conservation of mass, temperature, viscosity, etc. of the solute. Models employed in methods for determining diffusivity by measuring concentration at only one location or by measuring the concentration of sample material in a constant stream do not always provide for those parameters. Other advantages of the disclosed methods over previous methods include the capability to simultaneously calculate average velocity and molecular diffusivity.

DETAILED DESCRIPTION OF THE INVENTION

The invention can be used in any fluid channel where the Taylor-Aris dispersion model applies, i.e. where the rate of molecular diffusion across a channel is equivalent to or faster than the rate at which the molecules flow down the channel. As is understood by one skilled in the art, for a fixed velocity, the smaller the cross sectional area of the channel the more applicable the Taylor-Aris dispersion model. As explained by that model, the relatively rapid diffusion mitigates the dispersal of a pulse of material caused by a parabolic flow profile. Because of the small cross-sectional areas of microfluidic channels, the Taylor-Aris dispersion model typically applies to those channels.

When analyzing interactions between molecules in liquid media as the liquid media flows through a channel, a suitable channel can be a microchannel, or a channel of even smaller cross-sectional area. As used herein, the term "microscale", "microfluidic", or "microchannel" generally refers to structural elements or features of a device that have at least one fabricated dimension in the range of from about 0.1 micrometer to about 500 micrometers. Microscale fluidic elements such as channels, passages, chambers, or conduits have at least one internal cross-sectional dimension, such as depth, width, length, or diameter, that is less than 500 micrometers, and typically between about 0.1 micrometer and about 500 micrometers. In an embodiment of the invention, the microscale channels, passages, chambers or conduits preferably have at least one cross-sectional dimension between about 0.1 micrometer and 200 micrometers. The microfluidic devices or systems used in accordance with the present invention typically include at least one microscale channel. However, the devices or systems may include two or more microchannels, or even two or more intersecting microchannels, within a single body structure. Channel intersections may exist in a number of formats, including cross intersections, "T" intersections, or any number of other structures whereby two or more channels are in fluid communication.

However, it should be understood that embodiments of the invention could be applied to channels that are larger than a microchannel, provided that the flow conditions and channel geometry are compatible with the Taylor-Aris dispersion model. In some embodiments, for example, methods in accordance with the invention could be applied to molecules in the gaseous phase. Also, channels with a variety of cross sectional shapes are compatible with embodiments of the invention. Examples of channel cross sectional shapes compatible with embodiments of the invention include channels with circular, oval, elliptical, square, and rectangular cross sections.

In some embodiments of the invention, the amount of dispersion is measured by detecting the concentration profile of one or more molecules flowing through a channel. Any means known to one of skill in the art may be used to detect the presence or concentration of the molecules within the channel. These means may include optical methods such as absorbance or fluorescence spectroscopy, thermal lens spectroscopy (see e.g., Kitamori et al., *Jpn. J. Appl. Phys.* 39, 5316–5322, (2000)), UV spectroscopy; electrochemical methods such as potentiometric and ampiometric detection; and other physical methods and chemical methods such as mass spectroscopy, magnetic resonance techniques such as nuclear magnetic resonance or electron paramagnetic resonance, and radioactive measurement. The preferred embodiments employ fluorescence or absorbance spectroscopy to determine concentration profiles.

In embodiments involving optical methods of measuring concentration profiles, microfluidic devices in accordance with the invention typically include at least two optical detection windows disposed across one or more channels of the device. The optical detection windows are transparent to the relevant wavelength of light so that they are capable of transmitting an optical signal from the channel across which they are disposed. The optical detection windows can be a region of a transparent cover layer, or a transparent window within an opaque cover layer. For example, if the optical detection is carried out using UV light, the transparent cover layer or transparent region of the cover layer may be fabricated from quartz. Depending on the wavelength of light being used to carry out the optical detection, the appropriate optical detection window material might be glass or quartz, or a transparent polymer material such as PMMA or polycarbonate. Suitable optical detection techniques include, but are not limited to, absorbance or fluorescence spectroscopy, thermal lens spectroscopy and UV spectroscopy.

Microfluidic devices in accordance with the invention may include multiple sample introduction ports or reservoirs for the parallel or serial introduction and analysis of multiple samples. Examples of devices compatible with embodiments of the invention are described in U.S. Pat. No. 5,976,336, which is incorporated herein by reference in its entirety. Alternatively, these microfluidic devices may be coupled to a sample introduction port, such as a pipettor, which serially introduces multiple samples into the device for analysis. Examples of such sample introduction systems are described in U.S. Pat. Nos. 6,046,056 and 5,880,071, which are herein incorporated by reference in their entireties.

Methods in accordance with the invention involve the injection and flow of an aliquot of sample material (a "plug") into and through a microscale fluidic channel. The channel may exist as a discrete channel, such as a capillary or tube into which a sample material is introduced, or as a channel in a microfluidic device.

Sample plugs subjected to pressure-driven flow in microfluidic channels spread via Taylor-Aris dispersion, in which the dispersivity, or dispersion coefficient, is inversely proportional to the molecular diffusivity. The computer-controlled application of pressure to the channels in a microfluidic device may be used to gain precise control over fluid motion in the microfluidic channel network of the device. A suitable pressure control system is described in U.S. Patent Application Publication No. US 2001/0052460, which is incorporated by reference herein in its entirety. Although embodiments of the invention are most obviously applicable to pressure-driven flow, which is the type of flow for which the Taylor-Aris dispersion model was developed, embodiments of the invention are also applicable any flow to which the Taylor-Aris model is applicable. Among the requirements for the Taylor-Aris model to apply to a particular flow are that the flow be unidirectional and deterministic. Thus, for example, the Taylor-Aris model could apply to a flow through a microfluidic channel that is driven by a combination of pressure and electrokinetic forces.

Figure 1:
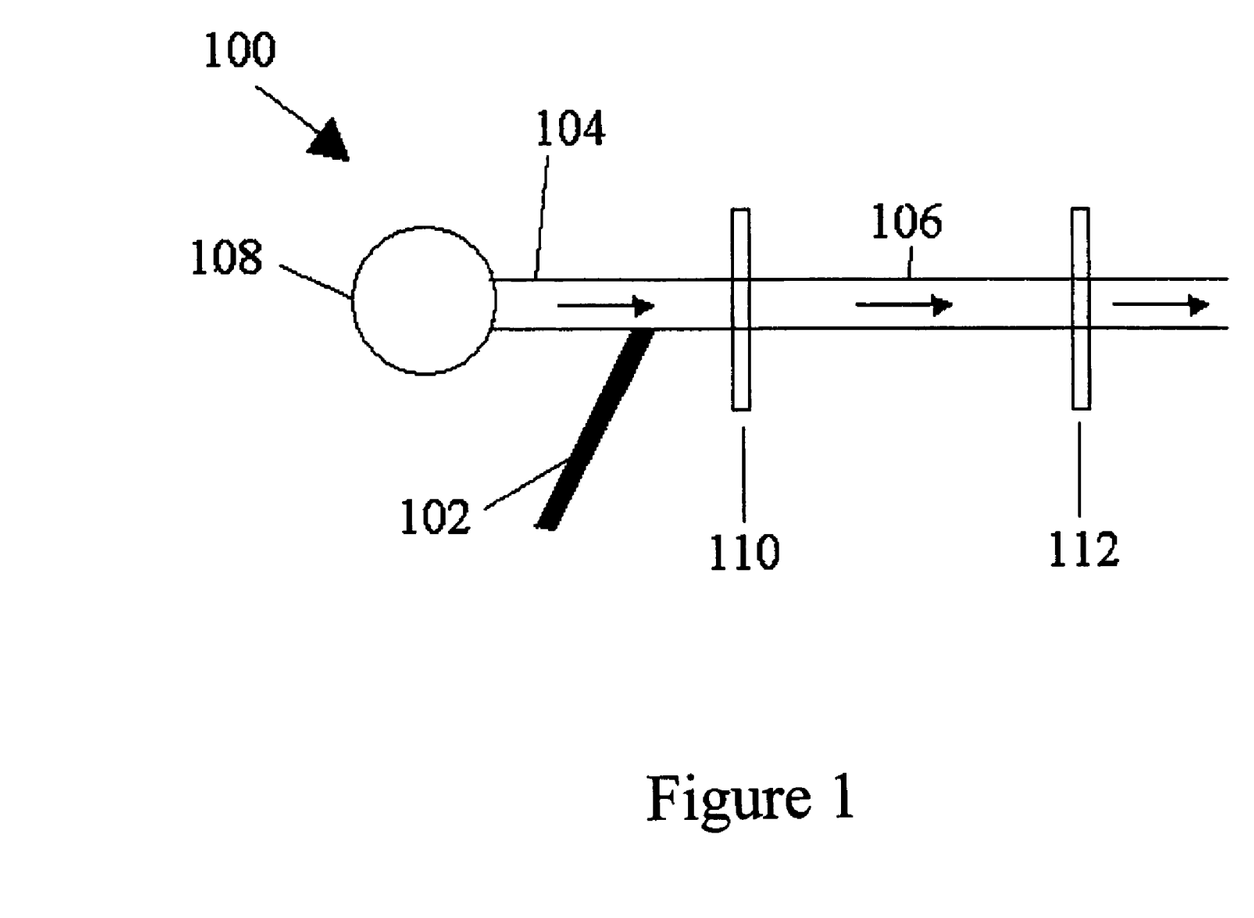
FIG. 1 is a microchannel of a microfluidic device.

An illustrative embodiment of the invention involves a molecular binding assay carried out in a single channel microfluidic device. An example of a microfluidic device with a single channel configuration suitable for use in embodiments of the present invention is shown in FIG. 1. The microfluidic device 100 includes a pipettor element or a sampling element (a "sipper") 102, a main channel 106, and a portion 104 of the main channel 106 that lead to a reservoir 108. In this particular design, a solution containing a small molecule can be drawn into the sipper 102 and then into main channel 106, while a buffer solution flows from reservoir 108, via channel portion 104, in a steady manner into the main channel 106. The "single channel" in the embodiment of FIG. 1 is the single main channel 106 in which the dispersion of the molecules is measured.

As discussed above, a variety of detection methods can be used to detect the concentration of one or more molecules. In the example embodiment of FIG. 1, the sample molecules introduced through sipper 102 can be fluorescently labeled so that they can be detected using optical detectors 110 and 112. Detectors 110 and 112 can be any distance apart from each other along the length of the channel. Consequently, both short-term and long-term dispersivity can be measured and evaluated. The short-term dispersivity can be used to evaluate K.

In embodiments of the invention, the molecular diffusivity can be obtained by measuring a first and a second experimental concentration profile of the same plug of material in at least two different locations along the length of the channel. For example, in the embodiment of FIG. 1, a first concentration profile of a plug of material introduced through sipper 102 is measured in the portion of channel 106 sampled by detector 110, and a second concentration profile of the material is measured in the portion of channel 106 sampled by detector 112. It may be preferable to employ detectors capable of simultaneously detecting the entire concentration profile of the material. This could be accomplished by having each detector comprise an array of sensors. In the embodiment of FIG. 1, this could be accomplished by having detectors 110 and 112 be CCD cameras. Alternatively, the detectors employed in embodiments of the invention could comprise a single sensor that determines the concentration profile by sampling a single location in the channel as the plug of material passes that point. Such a single sensor detector could be employed if the time required to measure the entire concentration profile of a plug of material, which is the time it takes the plug to flow past the location of the single sensor, is short compared to the time scale of the dispersion of the pulse.

The first concentration profile obtained at the first, most upstream, measurement location, which is adjacent to detector 110, can be modeled as a first Gaussian curve. An estimate for a second Gaussian curve that describes the concentration profile at the second, downstream, measurement location adjacent to detector 112 can then be derived. The estimate for the second concentration profile, which is a function of the unknown Taylor-Aris dispersion coefficient K, can then be compared to the actual second concentration profile measured by detector 112. The value of K that minimizes the difference between the estimated second concentration profile and the actual second concentration profile can then be determined. This value of K allows one skilled in the art to solve for the molecular diffusivity D.

In a first embodiment of the just-described calculation of the molecular diffusivity from the Taylor-Aris dispersion coefficient, the estimate for the second concentration profile is derived from a convolution calculation. The first, most upstream, measurement location, which is adjacent to detector 110 in FIG. 1, is a distance $x_0$ from the insertion point. The first concentration profile $f_0(x, \tau_0)$ is measured at the first measurement location at a time $\tau_0$. At time $\tau_0$ the centroid of the concentration profile $f_0(x, \tau_0)$ is located at $x_0$, and the variable x is measured with respect to the centroid. A second measurement location is a distance $x_1$ from the insertion point. The distance $x_1$ is greater that the distance $x_0$, so the second measurement location is downstream of the first measurement location. A second concentration profile $f_1(x, \tau_1)$ is measured at the second measurement location at a time $\tau_1$, which is later than time $\tau_0$. As with the first concentration profile, the variable x is measured with respect to the centroid of the pulse, which is at $x_1$ at time $\tau_1$. An average velocity of the plug of material can be calculated by measuring the time and distance between the first and second locations. In other words, the average velocity is $U=(x_1-x_0)/(\tau_1-\tau_0)$. The concentration profile at the first location $f_0(x, \tau_0)$ can be convoluted to determine a theoretical concentration profile at the second location $f_1'(x, \tau_1)$ using the following Green's function equation:

$$f_1'(x, \tau_1) = f_0(x, \tau_0) * \frac{1}{\sqrt{4\pi K(\tau_1 - \tau_0)}} \exp\left(\frac{-x^2}{4K(\tau_1 - \tau_0)}\right)$$

where * is the convolution operator.

Since the molecular diffusivity would be correct where the theoretical concentration profile at the second location $f_1'(x,\tau_1)$ is equal to the experimental concentration profile at the second location $f_1(x,\tau_1)$, the theoretical concentration profile at the second location $f_1'(x,\tau_1)$ can be set equal to the experimental concentration profile at the second location $f_1(x,\tau_1)$, as in the following equation:

$$f_1(x_1, \tau_1) = f_1'(x_1, \tau_1) = f_0(x_0, \tau_0) * \frac{1}{\sqrt{4\pi K(\tau_1 - \tau_0)}} \exp\left(\frac{-x^2}{4K(\tau_1 - \tau_0)}\right)$$

Using this equation to obtain a value for K, and then solving the appropriate Taylor-Aris dispersion coefficient formula for D, would provide the molecular diffusivity for the sample material.

In a second embodiment of the previously described calculation of the molecular diffusivity from the Taylor-Aris dispersion coefficient, an expression for the error in the estimate of the second concentration profile is employed. A value of the Taylor-Aris dispersion coefficient K is derived by minimizing this expression for the error in the estimate. The expression for the error in the estimate of the second concentration profile is:

$$\text{error} = \int_{-\infty}^{\infty} \left( \int_{-\infty}^{\infty} f_0(x-\xi) \frac{1}{\sqrt{4\pi K(\tau_1 - \tau_0)}} \exp\left\{\frac{-\xi^2}{4K(\tau_1 - \tau_0)}\right\} d\xi - f_1(x) \right) dx$$

Those skilled in the art will be familiar with a variety of methods for deriving the value of K that minimizes this expression for error. For example, the method could be as simple as deriving the value of K that minimizes the expression for error by trial and error. In any case, once the value of K has been determined, the molecular diffusivity D can then be found by solving the appropriate Taylor-Aris dispersion coefficient formula for D. Such a formula would have to be determined numerically or experimentally using a standard of known diffusivity.

In another embodiment, the Taylor-Aris dispersion coefficient can calculated in a method that does not require convolution. As in the two previously described embodiments that employ convolution calculations, the concentration profile of the plug is measured at two locations along the channel. A first concentration profile $f_0(x, \tau_0)$ is measured at time $\tau_0$ at a first measurement location a distance $x_0$ from the insertion point, and a second concentration profile $f_1(x, \tau_1)$ is measured at time $\tau_1$ at a second measurement location a distance $x_1$ from the insertion point. The distance $x_0$ is less than the distance $x_1$, and the time $\tau_0$ occurs before the time $\tau_1$. As previously discussed, a sharp plug of sample material inserted into a stream of flowing fluid that is subject to Taylor-Aris dispersion produces a concentration profile that resembles a Gaussian curve. The variance $\sigma^2$ for a Gaussian concentration profile resulting from Taylor-Aris dispersion is $2K\tau$. Thus the difference between the variance $\sigma_0^2$ of the concentration profile $f_0(x, \tau_0)$ and the variance $\sigma_1^2$ of the concentration profile $f_1(x, \tau_1)$ is:

$$\sigma_1^2 - \sigma_0^2 = 2K(\tau_1 - \tau_0)$$

Therefore the Taylor-Aris dispersion coefficient K can be calculated by simply finding the difference in variance between the variances for the concentration profiles $f_0(x, \tau_0)$ and $f_1(x, \tau_1)$. Then, as in all of the methods, the molecular diffusivity D can then be found by solving the appropriate Taylor-Aris dispersion coefficient formula for D. If the first concentration profile $f_0(x, \tau_0)$ and the second concentration profile $f_1(x, \tau_1)$ are approximately Gaussian, then the variances $(\sigma_0^2, \sigma_1^2)$ of the two distributions can be easily calculated using well known methods of determining the variances of the Gaussian curves. If the first and second concentration profiles are not approximately Gaussian, then more generally applicable methods of determining the variance of a function can be employed. For example, the variance of a concentration profile c(x) can be calculated by first determining the center of mass $x_{cm}$ of the profile:

$$x_{cm} = \int_{-\infty}^{\infty} \frac{x \cdot c(x)}{\int_{-\infty}^{\infty} c(x) dx} dx,$$

and then determining the variance of the concentration profile $\sigma^2$ from the standard definition of variance:

$$\sigma^2 = \int_{-\infty}^{\infty} \frac{(x - x_{cm})^2 c(x)}{\int_{-\infty}^{\infty} c(x) dx} dx.$$

The mathematical models employed in the disclosed methods of measuring and comparing the concentration profiles of a single plug at two different locations automatically take into account such physical parameters as the conservation of mass, temperature, viscosity, etc. of the solute. Those parameters are taken into account largely by virtue of the fact that the concentration profile of the pulse is measured at two locations, and that the models basically look at the difference between the two profiles. This comparison calculation eliminates the need to evaluate those physical parameters. Contrast this with prior art methods that rely on a single measurement of concentration profile where those parameters must be estimated, introducing another source of error into the calculation of molecular diffusivity.

The method of the present invention can be used with sample solutions and buffer solutions of any viscosity and at any temperature. Because the present invention utilizes concentration profiles at more than one location along the length of the channel, velocity anomalies may be detected. A measured concentration profile that is non-Gaussian could be evidence that the solute is sticky and not flowing at a constant and controlled rate throughout the length of the tube. For example, a concentration profile of a solute with a "tail" that increases in length at each subsequent measurement of the concentration profile would be evidence of non-equilibrium sticking of the solute. Irregularities in flow rates may not otherwise be detectable if only a singular measurement of the concentration profile of a pulse is taken.

In other embodiments of the invention, the concentration profile of a pulse may be measured at more than two locations in a channel. Also, the concentration profile of a pulse may be measured using different detection techniques during the course of a single experiment. Embodiments of the invention could also include devices that measure the concentration profile at two points along a channel by having the channel pass under a detector more than once.

The present invention is particularly well suited to biological materials, compounds and molecules, such a DNA, the molecular diffusivities of which have yet to be determined by experimental means.

EXAMPLES

The following examples are provided to further illustrate the present invention. It is to be understood, however, that these examples are for purposes of illustration only and are not intended as a definition of the limits of the invention.

Figure 2:
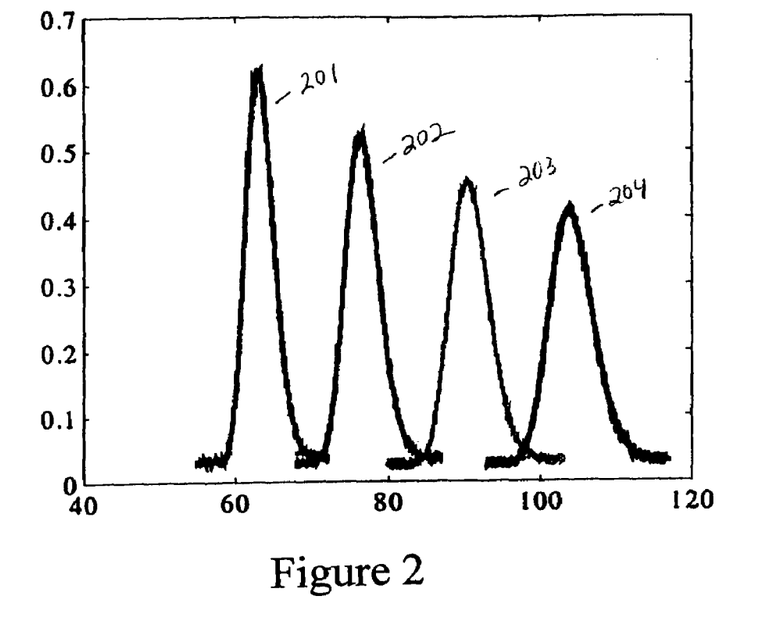
FIG. 2 is a graph depicting four Gaussian shaped concentration profiles taken at four locations along the length of a microchannel.

A one-second plug of 1 µM fluorescein dye solution was introduced into a detection channel of a SP-384 sipper chip (available from Caliper Technologies Corp., Mountain View, Calif.). Upon introduction to the channel, the plug of fluorescein dye was added to a buffer solution stream. The intensity of the fluorescein dye was monitored and measured by a Caliper 220 detection platform (available from Caliper Technologies Corp., Mountain View, Calif.) having 520 nm emission filters and 488 nm laser excitation for fluorescence measurements. The measurements took place at four points along the length of the detection channel. FIG. 2 shows concentration profiles measured at four locations that have been mapped together on a single graph for comparison. These four concentration profiles are labeled 201, 202, 203 and 204, respectively, wherein concentration profile 201 was measured at a location closer to the insertion point of the plug than the location where concentration profile 202 was measured, and so on.

Example 1

Figure 3:
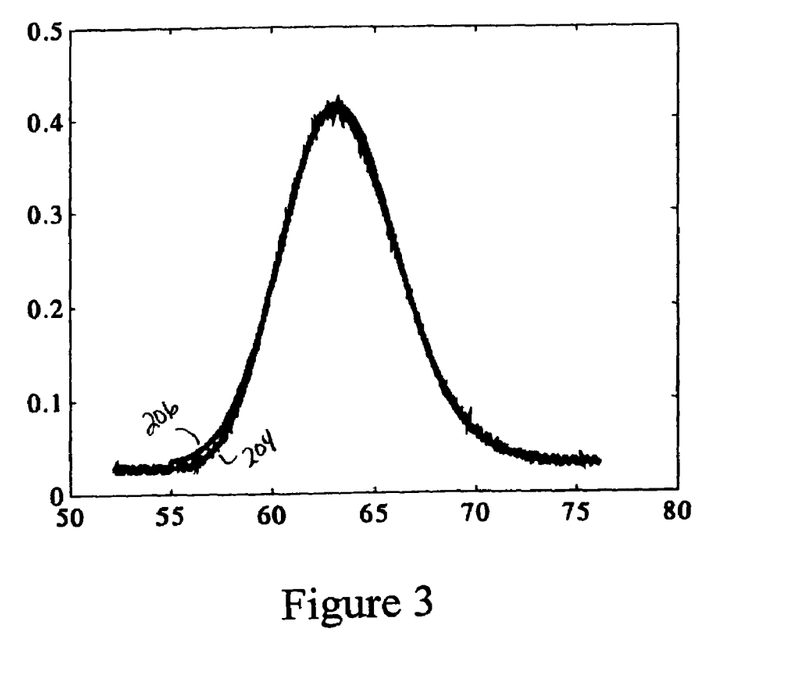
FIG. 3 is a graphical comparison of a theoretical concentration profile convoluted using the steps of the present invention and an experimental concentration profile.
Figure 4:
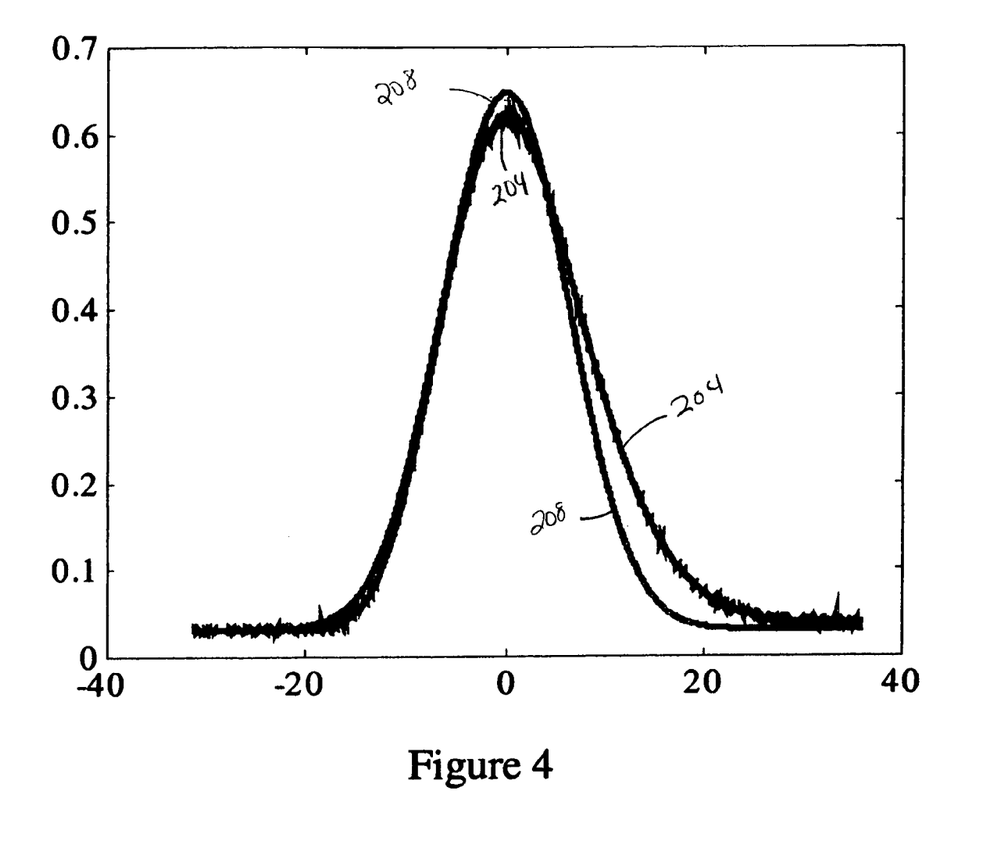
FIG. 4 is a graphical comparison of a theoretical concentration profile convoluted using the steps of the present invention and an experimental concentration profile.

In this example, the diffusivity was determined based on data detected at a first and fourth detector (i.e., concentration profiles 201 and 204, respectively). However, any two of the concentration profiles of FIG. 2 could be used in the same manner described below. The first concentration profile 201 was modeled using an expression for Gaussian curve $f_1(x, \tau_1)$. The expression $f_1(x,\tau_1)$ was convoluted using the Green's function to create an estimate $f_4'(x,\tau_4)$ for the concentration profile measured by the fourth detector. A value of the Taylor-Aris dispersion coefficient K was then derived by setting the expression for the estimated concentration profile $f_4'(x,\tau_4)$ equal to the measured concentration profile $f_4(x,\tau_4)$. FIG. 3 shows that the estimated concentration profile $f_4'(x,\tau_4)$ 204 calculated using the derived value of K is essentially identical to the actual measured concentration profile $f_4(x,\tau_4)$ 206. Once the Taylor-Aris diffusion coefficient K was found, the molecular diffusivity was calculated from the following equation:

$$K = D\left(1 + \frac{1}{210} f\left(\frac{d}{w}\right) \frac{U^2 d^2}{D^2}\right)$$

wherein the function $f(d/w)$ for the particular microchannel is $7.9512 - 13.594\ (d/w) + 10.542\ (d/w)^2 - 3.174\ (d/w)^3$, U is the average velocity and D is the molecular diffusivity. The molecular was determined to be around 330 $\mu m^2/s$. FIG. 4 shows a comparison between an estimated concentration profile $f_4'(x,\tau_4)$ 208 wherein the molecular diffusivity is presumed to be equal to about 400 $\mu m^2/s$ and the measured concentration profile $f_4(x,\tau_4)$ 204. The difference between the profiles is more obvious than the difference shown in FIG. 3.

Example 2

Figure 5:
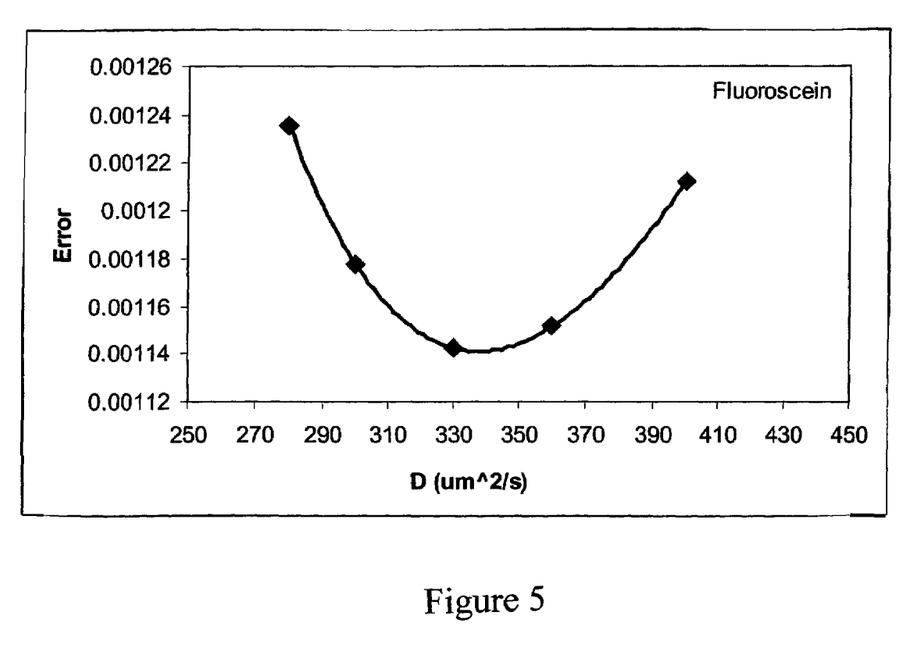
FIG. 5 is a graph depicting calculated error at various assumed diffusivities.

For this second example, the Taylor-Aris dispersion coefficient is calculated by minimizing the value of an expression for the error in an estimated concentration profile. The error was determined by assuming a value of molecular diffusivity D, calculating the corresponding value of K, and inserting that value of K into the previously presented expression for error. To determine the value of D at which the error is minimized, the value of the error is plotted in FIG. 5 as a function of D. The correct value for the molecular diffusivity for the fluorescein dye was determined by finding the lowest point of the curve, where the error is at a minimum (i.e., where the estimated concentration profile $f_4'(x,\tau_4)$ most closely matches the measured concentration profile $f_4(x,\tau_4)$. The value of D at the minimum error is approximately 330 $\mu m^2/s$. This value of D agrees closely with the value of D calculated in the previous example.

It will be apparent to those skilled in the relevant art that the disclosed invention may be modified in numerous ways and may assume embodiments other than the preferred form specifically set out and described above. Accordingly, it is intended by the appended claims to cover all modifications of the invention that fall within the true spirit and scope of the invention.

What is claimed is:

1. A method for calculating the diffusivity of a solute in a microchannel, the method comprising the steps of:
   providing a microchannel having a first end and a second end and a cross-sectional shape;
   providing a first detector and a second detector that measure the concentration of solute at a first location and a second location respectively, the first and second locations being disposed between the first and second ends of the microchannel;
   introducing the solute into the first end of said microchannel as a plug;
   measuring a first concentration profile of the plug at the first location at a first time;
   measuring a second concentration profile of the plug at the second location at a second time;
   calculating a velocity based on a distance between the first location and the second location and the first and second times; and
   determining the diffusivity of the solute by comparing the first concentration profile to the second concentration profile.

2. The method of claim 1, wherein the plug disperses in a manner consistent with the Taylor-Aris dispersion model, forming a Gaussian shaped concentration profile as it flows through the microchannel, the Gaussian shaped concentration profile comprising a centroid.

3. The method of claim 2, wherein the first time is the time at which the centroid of the plug is present at the first location, and the second time at which the centroid of the plug is present at the second location.

4. The method of claim 1, wherein the first and second detectors are capable of measuring the first and second concentration profiles respectively in a single measurement.

5. The method of claim 1, wherein the first and second detectors measure the first and second concentration profiles by repeatedly sampling respective single locations as the respective concentration profiles move past those respective locations.

6. The method of claim 1, wherein the step of determining the diffusivity of the solute by comparing the first concentration profile to the second concentration profile comprises computing an estimated second concentration profile from the first concentration profile, setting the estimated second concentration profile equal to the second concentration profile in an equation, solving the equation for the Taylor-Aris dispersion coefficient, and solving for diffusivity from the definition of the Taylor-Aris dispersion coefficient appropriate for the cross-sectional shape of the microchannel.

7. The method of claim 1, wherein the step of determining the diffusivity of the solute by comparing the first concentration profile to the second concentration profile comprises computing an error in an estimated second concentration profile based on the first concentration profile, determining the value of the Taylor-Aris dispersion coefficient that minimizes the error, and solving for diffusivity from the definition of the Taylor-Aris dispersion coefficient appropriate for the cross-sectional shape of the microchannel.

8. The method of claim 1, wherein the step of determining the diffusivity of the solute by comparing the first concentration profile to the second concentration profile comprises computing a first variance $\sigma_1$ for the first concentration profile, computing a second variance $\sigma_2$ for the second concentration profile, solving for the Taylor-Aris dispersion coefficient K from the expression $\sigma_2^2 - \sigma_1^2 = 2K(\tau_2 - \tau_1)$, where $\tau_1$ and $\tau_2$ represent the first and second times, and solving for diffusivity from the definition of the Taylor-Aris dispersion coefficient appropriate for the cross-sectional shape of the microchannel.

9. A method for measuring an average velocity of a solute in a microchannel comprising:
   providing a microchannel;
   introducing a solute at one end of said microchannel;
   measuring a first concentration profile at a first upstream location along said microchannel;

determining a first time at which a feature of the first concentration profile arrives at the first upstream location;

measuring a second concentration profile at a second downstream location along said microchannel;

determining a second time at which the feature of the second concentration profile arrives at the second downstream location; and calculating the average velocity of said plug between said first and said second location a velocity based on a distance between the first location and the second location and the first and second times.

10. The method of claim 9, wherein the feature is the centroid of a Gaussian curve.

* * * * *